(12) United States Patent
Bruder et al.

(10) Patent No.: US 8,605,977 B2
(45) Date of Patent: Dec. 10, 2013

(54) ITERATIVE CT IMAGE FILTER FOR NOISE REDUCTION

(75) Inventors: Herbert Bruder, Höchstadt (DE); Rainer Raupach, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 673 days.

(21) Appl. No.: 12/874,302

(22) Filed: Sep. 2, 2010

(65) Prior Publication Data
US 2011/0052030 A1 Mar. 3, 2011

(30) Foreign Application Priority Data
Sep. 3, 2009 (DE) .......................... 10 2009 039 987

(51) Int. Cl.
*G06K 9/00* (2006.01)
(52) U.S. Cl.
USPC .......................................................... 382/131
(58) Field of Classification Search
None
See application file for complete search history.

(56) References Cited

U.S. PATENT DOCUMENTS

| | | | |
|---|---|---|---|
| 4,825,297 A | | 4/1989 | Fuchsberger et al. |
| 2006/0133689 A1* | | 6/2006 | Andersson et al. ........... 382/261 |
| 2007/0196008 A1* | | 8/2007 | Borsdorf et al. .............. 382/131 |

FOREIGN PATENT DOCUMENTS

DE 3629409 A1 8/1986

OTHER PUBLICATIONS

Pietro Perona and Jitrendra Malik; Scale-Space and Edge Detection Using Anisotropic Diffusion; IEEE Transactions on Pattern Analysis and Machine Intelligence, vol. 12. No. 7. Jul. 1990; p. 629-639.; Book; 1990.
German Office Action.

* cited by examiner

*Primary Examiner* — Claire X Wang
(74) *Attorney, Agent, or Firm* — Harness, Dickey & Pierce, P.L.C.

(57) ABSTRACT

A method is disclosed for reconstruction of image data of an examination object from measured data, wherein the measured data was captured during a relative rotational motion between a radiation source of a computed tomography system and the examination object. Image data of the examination object is determined from the measured data. In at least one embodiment, new image data is obtained by noise-reducing processing of the image data, in which weighted high-pass filtering of the image data is performed, the weighting taking account of differences between pixel values of different pixels such that increasing differences result in a weaker high-pass effect. A noise-reducing smoothing of the image data is performed using the weighted high-pass filtering.

25 Claims, 7 Drawing Sheets

ITERATIVE CT IMAGE FILTER FOR NOISE REDUCTION

PRIORITY STATEMENT

The present application hereby claims priority under 35 U.S.C. §119 on German patent application number DE 10 2009 039 987.9 filed Sep. 3, 2009, the entire contents of which are hereby incorporated herein by reference.

FIELD

At least one embodiment of the invention generally relates to a method for reconstruction of image data of an examination object from measured data, the measured data having been captured during a relative rotational motion between a radiation source of a computed tomography system and the examination object.

BACKGROUND

Methods for scanning an examination object with a CT system are generally known, with use being made, for example, of circular scans, sequential circular scans with feed or spiral scans. During these scans absorption data on the examination object is captured from different capture angles using at least one x-ray source and at least one opposed detector, and the absorption data or projections collected in this way are allocated to sectional views through the examination object by way of corresponding reconstruction methods.

For reconstruction of computed-tomography images from x-ray CT datasets of a computed tomography device (CT device), i.e. from the projections captured, use is made nowadays of what is known as a Filtered Back Projection (FBP) method as a standard method. Following the data capture, what is known as a "rebinning" step is carried out, in which the data generated with the fan-shaped beam extending from the source is rearranged so that it is present in a form as if the detector was being hit by x-rays approaching the detector in parallel. The data is then transformed into the frequency range. Filtering takes place in the frequency range, and then the filtered data is transformed back. A back projection onto the individual voxels within the volume of interest is then performed using the thus rearranged and filtered data. In traditional FBP methods the image definition is linked to the image noise. The higher the definition achieved, the higher the image noise too, and vice versa.

While the CT-measured data is being captured, the examination object, generally a patient, is exposed to a dose of x-ray radiation. Since this radiation is generally not harmless for the examination object an effort is made to get by with the least possible radiation exposure. The dose used is however directly linked to the image noise in the image data reconstructed from the CT-measured data: a reduction in the dose leads to an increase in the noise. To make maximum use of a particular radiation dose it is therefore worthwhile to use image reconstruction methods which efficiently reduce the noise in CT images.

SUMMARY

In at least one embodiment of the invention demonstrates a method for reconstruction of CT images which should have little noise. Furthermore, in at least one embodiment a corresponding control and computing unit, a CT system, a computer program and a computer program product should be demonstrated.

The method of at least one embodiment is for reconstruction of image data of an examination object, based on measured data which was captured during a relative rotational motion between a radiation source of a computed tomography system and the examination object. Image data of the examination object is determined from the measured data. New image data is obtained by noise-reducing processing of the image data, in which weighted high-pass filtering of the image data takes place, the weighting taking account of differences between pixel values of different pixels such that increasingly larger differences result in a weaker high-pass effect. A noise-reducing smoothing of the image data is effected using the weighted high-pass filtering.

Image data is thus initially reconstructed. Consequently an image of the examination object already exists. To calculate the image from the measured data use can be made here of known reconstruction methods, in particular a filtered back projection method. The image can be two- or three-dimensional. This image is now processed in order to reduce the image noise.

The noise-reducing processing comprises at least two steps. First comes the weighted high-pass filtering of the image data. The effect of the weighting here is that there is a difference from normal high-pass filtering, e.g. using a Laplace filter. In the weighting differences are considered between pixel values of different pixels: depending on how different the pixel values of two pixels are, one of the pixels is used in the calculation of the high-pass filtered value of the other pixel to a greater or lesser extent. In this case an increasing difference results—at least in a particular value range of pixel value differences—in a weaker high-pass effect.

Once the weighted high-pass filtering has been calculated, a high-pass filtered image is produced. This is used to perform a noise-reducing smoothing of the image data and thus to obtain the new image data.

It is especially advantageous if the new image data is obtained by processing the image data without using the measured data. This is in contrast to an iterative reconstruction algorithm in which following an image calculation, projection data is calculated on the basis of this image and is compared with the measured data, in order to calculate new image data using an existing deviation between the calculated projection data and the measured data. In contrast, in the present case only the image data is required in order to calculate improved image data therefrom, without the measured data being considered afresh.

In one embodiment of the invention the new image data is output as results image data. The noise-reducing processing therefore already produces image data which no longer forms the basis of a further calculation to reduce the image noise. Alternatively, the new image data too can then be subjected to noise-reducing processing. This means that the same method steps which were performed previously on the basis of the image data for calculation of the new image data are now performed in order to further process the new image data.

In a development of at least one embodiment of the invention the noise-reducing smoothing is performed using weighted high-pass filtering, in that the high-pass filtered image data is subtracted from the image data. Weighting factors can if necessary be used to form this difference, i.e. the high-pass filtered image data can be multiplied by a factor which if necessary can differ from pixel to pixel, in order, having been multiplied in this way, to be subtracted from the image data. Subtracting high-pass filtered image data from the image data corresponds to a low-pass effect. A smoothing can be achieved in this way.

According to an especially preferred development of at least one embodiment of the invention, the weighting takes place by way of a function which initially ascends linearly and, as the argument increases, weaker than linearly. If the function is considered in the direction of its ascending argument, it is initially linear in the vicinity of the value 0 of the argument. Later, i.e. as the argument increases, the gradient of the function falls compared to the linear course. It is possible here that the function initially ascends linearly and, as the argument increases, weaker than linearly, and descends if the argument increases still further; in this case the gradient of the function therefore changes its sign. Furthermore it is possible that the function initially ascends linearly and, as the argument increases, weaker than linearly and descends if the argument increases still further and, if the argument increases still further, changes its sign. These different embodiments of the function make it possible to influence the differences between pixel values in a different way when weighting the high-pass filtering. Preferably the argument of the function to this end contains the difference between pixel values of two pixels. Moreover it is advantageous if the argument of the function contains or takes account of the noise at one of the two pixels.

In a development of at least one embodiment of the invention a variable is determined pixel by pixel which distinguishes between homogeneous areas and edges within the image data, and the variable decides pixel by pixel about the strength of use of the weighted high-pass filtering in the noise-reducing smoothing of the image data. An edge here means that a change from one type of tissue or material to a different type of tissue or material is present at the relevant point in the image, said change manifesting itself as a difference in the CT values. In this way the weighted high-pass filtering can, for each pixel, be used to a varying extent in the calculation of the new image, depending on whether it is located in a homogeneous area of an image or an area of an image with structure. In this case the variable need not, as a digital variable, decide between homogeneous area and edge; instead it is advantageous if it also indicates intermediate values.

According to one embodiment of the invention low-pass filtering takes place in addition to the noise-reducing smoothing, the variable deciding pixel by pixel on the strength of the low-pass filtering. Thus to reduce noise, not only is weighted high-pass filtering performed but low-pass filtering as well. The additional use of low-pass filtering takes place preferably by means of an addition. Because the variable decides on the degree to which the low-pass filtering is taken into account, the low-pass filtering can, for each pixel, be used in this way to a varying extent in the calculation of the new image, depending on whether it is located in a homogeneous area of an image or an area of an image with structure.

It is advantageous if the variable assumes values between 0 and 1, the value 0 corresponding to an edge and the value 1 to a homogeneous area. Based on the value of the variable it is possible to read whether a pixel is located in a homogeneous area of an image or an area of an image with structure: the bigger the value of the variable, the more homogeneous is the respective area of an image.

In an embodiment of the invention high-pass filtering of the image data and a pixel-by-pixel noise value determination are performed to calculate the variable. In this case the variable can be calculated by means of a Gaussian function, which for each pixel depends on a quotient of a high-pass filtered pixel value and a noise value.

According to a development of at least one embodiment of the invention the noise-reducing processing effects a contrast-dependent noise reduction of the image data. It is thus not smoothed equally across the entire image, which would cause definition to be lost; instead noise is removed in particular at low-contrast points of the image data, whereas in high-contrast points the aim is to retain the definition.

According to a development of at least one embodiment of the invention the image data is present as a temporal sequence of image data, and the noise-reducing processing is performed in the dimensions of both place and time. In this case the image data is three- or four-dimensional data, where one of these dimensions is time. This dimension can be treated in the same way as the two or three dimensions of space during noise-reducing processing of the image data.

The inventive control and computing unit of at least one embodiment is used to reconstruct image data of an examination object from measured data of a CT system. It includes a program memory for storing program code, and contains—among other things where appropriate—program code which is suitable for executing a method of the type described above. The inventive CT system includes such a control and computing unit. Furthermore it can contain other components which e.g. are required to capture measured data.

The inventive computer program of at least one embodiment has program code segments which are suitable for executing the method of the type described above if the computer program is executed on a computer.

The inventive computer program product of at least one embodiment includes, on a computer-readable data medium, stored program code means which are suitable for executing the method of the type described above if the computer program is executed on a computer.

BRIEF DESCRIPTION OF THE DRAWINGS

In the following the invention is described in greater detail on the basis of an example embodiment. The figures show.

DETAILED DESCRIPTION OF THE EXAMPLE EMBODIMENTS

Figure 1:
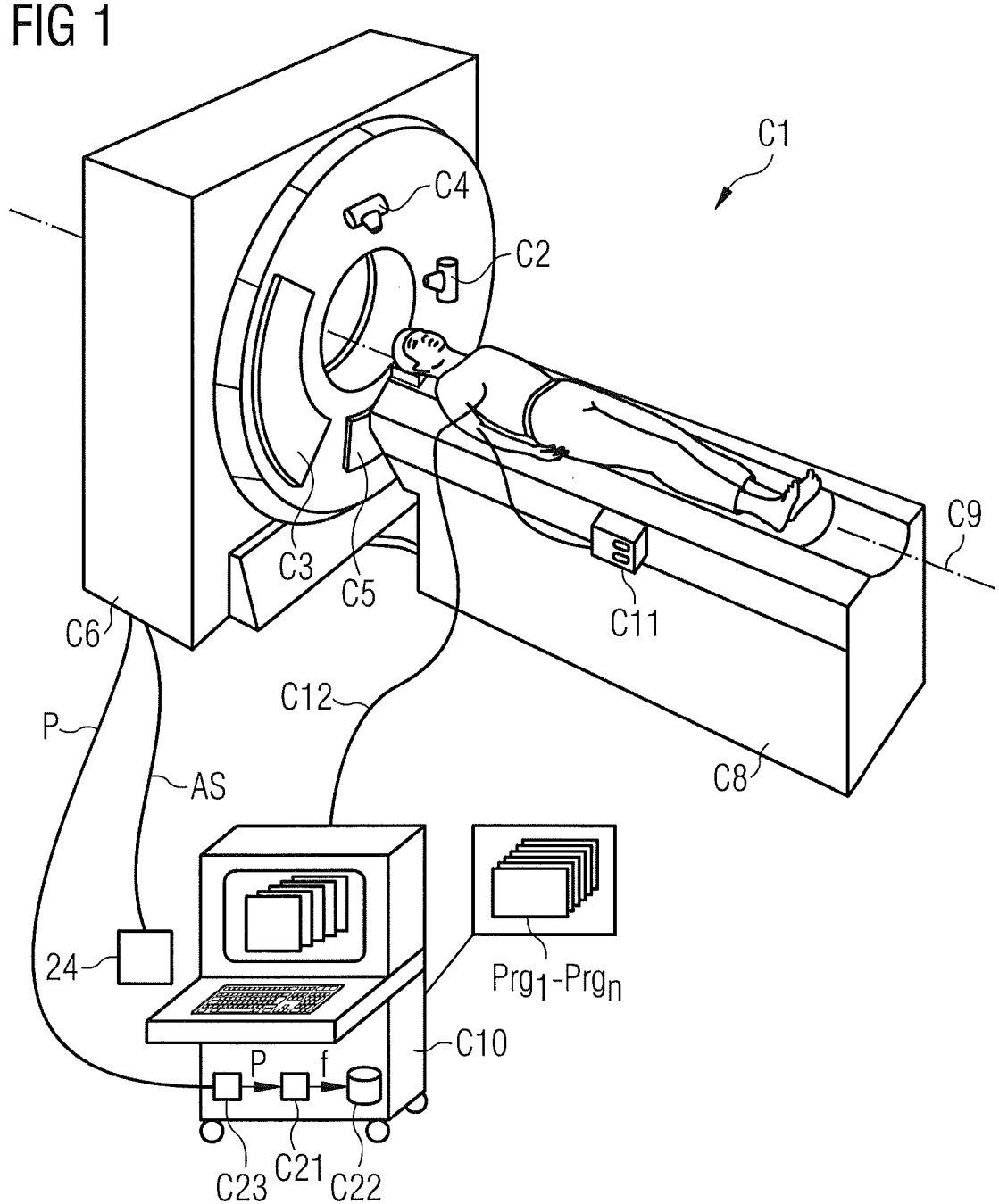
FIG. 1: a first diagrammatic representation of an example embodiment of a computed tomography system with an image reconstruction component.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 initially diagrammatically illustrates a first computed tomography system C1 with an image reconstruction unit C21. In the gantry housing C6 is a closed gantry (not shown here) on which a first x-ray tube C2 with an opposing detector C3 are arranged. Optionally a second x-ray tube C4 with an opposing detector C5 is disposed in the CT system shown here, so that thanks to the additionally available emitter/detector combination a higher time resolution can be achieved, or when using different x-ray energy spectra in the emitter/detector systems "dual-energy" examinations can also be performed.

The CT system C1 further has a patient couch C8, on which a patient can be pushed into the measurement field during the examination along a system axis C9, also known as the z-axis, it being possible for the scanning itself to take place both as a simple circular scan without patient feed exclusively in the examination area of interest. In this case the x-ray source C2 or C4 in each case rotates around the patient. The detector C3 or C5 moves in parallel here opposite the x-ray source C2 or C4, in order to capture projection measured data which is then used to reconstruct sectional views. Alternatively to a sequential scan, in which the patient is gradually pushed between the individual scans through the examination field, a spiral scan is of course also possible, in which the patient is pushed continuously along the system axis C9 through the examination field between x-ray tube C2 or C4 and detector C3 or C5 during the rotating scanning with x-ray radiation. Because of the motion of the patient along the axis C9 and the simultaneous rotation of the x-ray source C2 or C4 a helical path is produced in the case of a spiral scan for the x-ray source C2 or C4 relative to the patient during the measurement. This path can also be achieved by pushing the gantry along the axis C9 while the patient is stationary.

The CT system 10 is controlled by a control and computing unit C10 with computer program code $Prg_1$ to $Prg_n$ present in a memory. From the control and computing unit C10 acquisition control signals AS can be transmitted via a control interface 24, in order to control the CT system C1 in accordance with particular measurement protocols.

The projection measurement data p (also referred to in the following as raw data) acquired by the detector C3 or C5 is transferred via a raw data interface C23 to the control and computing unit C10. This raw data p is then further processed in an image reconstruction component C21, if necessary after suitable preprocessing. The image reconstruction component C21 is implemented in this example embodiment in the control and computing unit C10 in the form of software on a processor, e.g. in the form of one or more of the computer program codes $Prg_1$ to $Prg_n$. The image data f reconstructed by the image reconstruction component C21 is then stored in a memory C22 of the control and computing unit C10 and/or output in customary fashion on the monitor of the control and computing unit C10. It can also be fed via an interface not shown in FIG. 1 into a network connected to the computed tomography system C1, for example a radiological information system (RIS), and be stored in a mass memory which is accessible there or be output as images.

The control and computing unit C10 can additionally also perform the function of an ECG, a line C12 being used to dissipate the ECG potentials between patient and control and computing unit C10. Additionally the CT system C1 shown in FIG. 1 also has a contrast agent injector C11, via which contrast agent can additionally be injected into the patient's bloodstream, so that the patient's vessels, in particular the chambers of the beating heart, can be better represented. It is hereby also possible to perform perfusion measurements, for which the proposed method is likewise suitable.

Figure 2:
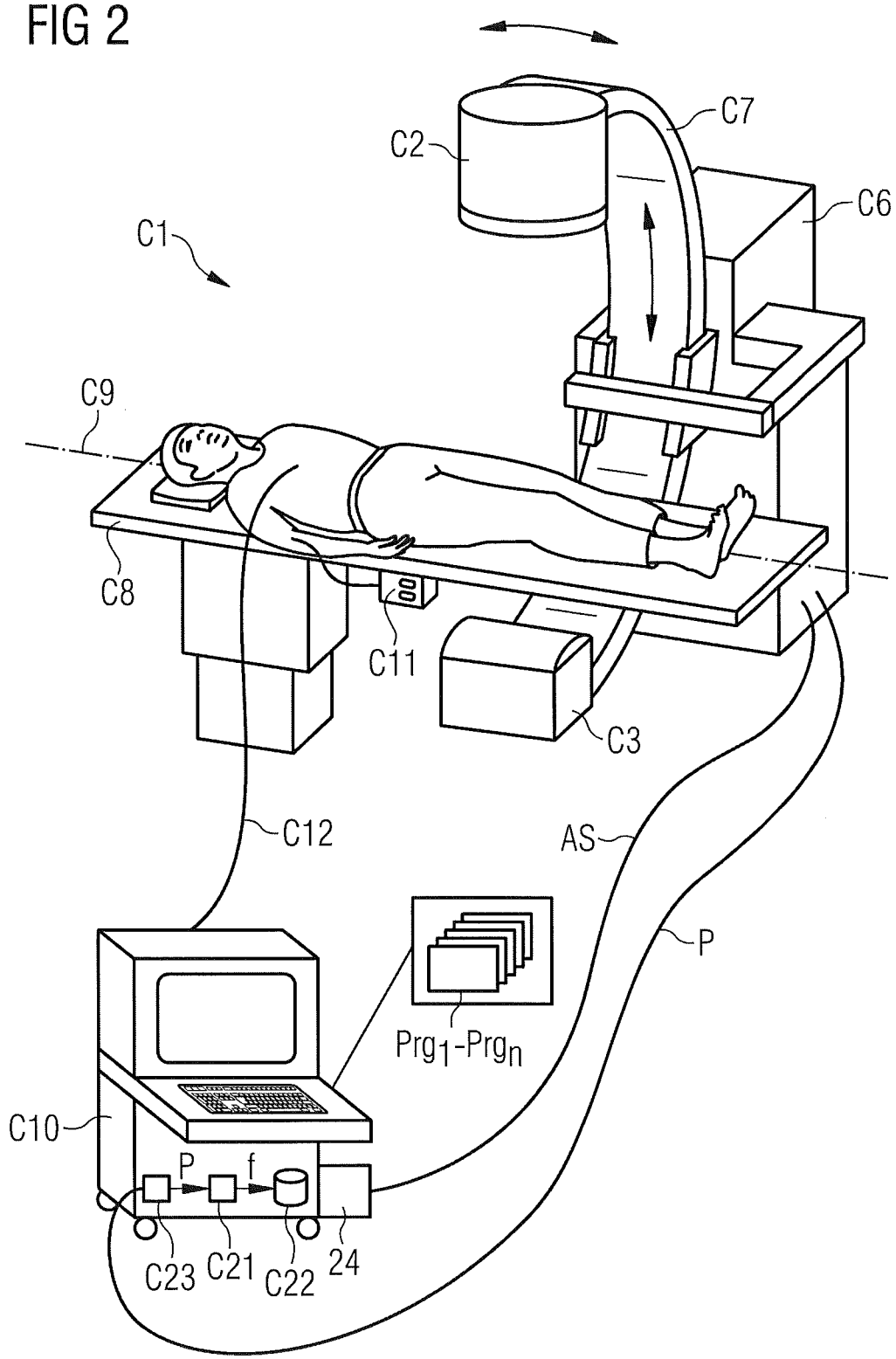
FIG. 2: a second diagrammatic representation of an example embodiment of a computed tomography system with an image reconstruction component.

FIG. 2 shows a C-arm system, in which in contrast to the CT system in FIG. 1 the housing C6 supports the C-arm C7, to which on one side the x-ray tube C2 and on the other side the opposed detector C3 are attached. The C-arm C7 is likewise swiveled about a system axis C9 for a scan, so that a scan can be performed from a multiplicity of scanning angles and corresponding projection data p can be determined from a multiplicity of projection angles. The C-arm system C1 in FIG. 2, like the CT system in FIG. 1, has a control and computing unit C10 of the type described for FIG. 1.

Embodiments of the invention can be used in both the systems shown in FIGS. 1 and 2. Furthermore it can in principle also be used for other CT systems, e.g. for CT systems with a detector forming a complete ring.

Since clinically relevant information is contained in the CT images reconstructed by the computing unit C10, it is especially important that these images are meaningful. For example, it should also be possible to identify small tumors in them, i.e. to distinguish them clearly from the surrounding tissue and for them to be identifiable as regards their size and position. Hence the aim is to undertake noise reduction in the CT images while simultaneously retaining or even increasing the visibility of detailed information. As a result, when the radiation dose is reduced the same image quality can be achieved, or in the case of the same dose a higher image quality.

In principle the noise in a CT image can be reduced by using smoothing image filters in the form of linear low-pass filters. However, a disadvantage here is that the image definition decreases at the same time, as a result of which detailed information is removed from the CT image. In order to assess the image definition, the steepness of an edge in a CT image can be considered which corresponds to an ideal edge discontinuity inside the real examination object. The steeper the edge inside the CT image, the more defined is the CT image. Smoothing performed on the basis of a noise reduction results in the edge being washed out, so that its steepness and thus the image definition decreases.

In the following, a method is described which reduces the noise of a CT image particularly efficiently. The method here contains the detailed information of the CT image, i.e. the definition is scarcely reduced, if at all. At the same time the area around edges is not excluded during noise reduction; instead the noise reduction is also effective in these areas of an image. Furthermore, the noise reduction method does not alter the typical CT noise texture. CT images in fact have a typical noise power spectrum, with which persons analyzing CT images, in particular radiologists, are familiar. Because of this familiarity or training effect it is undesirable to effect a fundamental change in the statistical attributes of the image noise.

Figure 3:
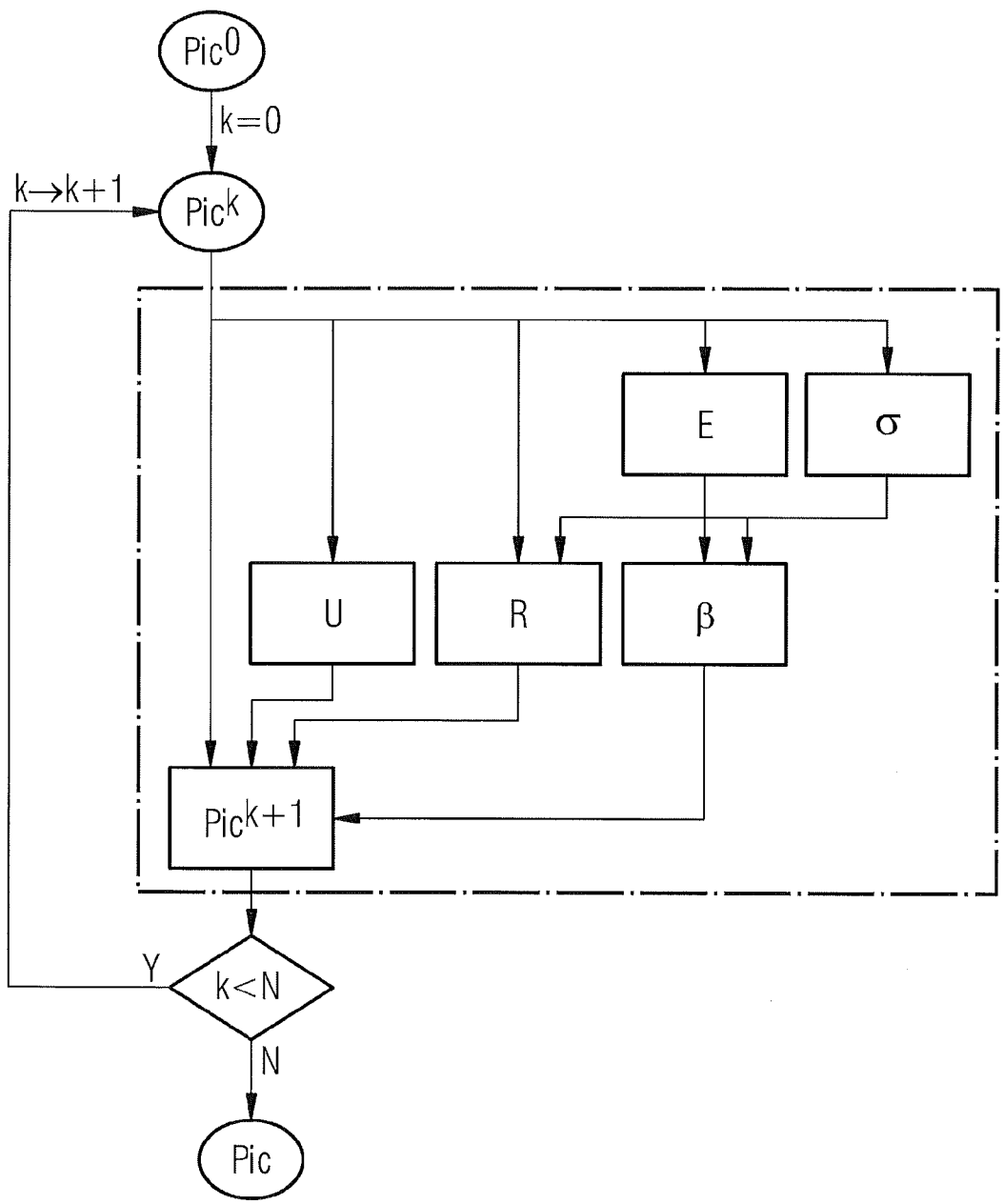
FIG. 3: a flow chart.

A flow chart of the method is shown in FIG. 3. At the start an initial image $Pic^0$ of the examination object is reconstructed from the measured data. The initial image $Pic^0$ is subsequently processed to reduce the noise. Multiple processing is performed, with the most recently obtained image in each case being used as the basis for the next processing. The image processing is thus iterative. The index 0 of the initial image $Pic^0$ shows that the image has not yet been subject to noise-reducing processing, it thus being the image of the 0-th iteration. Correspondingly the image $Pic^k$ is the image of the k-th iteration. The operations within an individual iteration are located in the dashed-line box in FIG. 3.

The images $Pic^0$ and $Pic^k$ can be two-dimensional layer images or three-dimensional volume images. In the former case a multiplicity of pixels is present, to which in each case an image value is assigned; in the second case a multiplicity of voxels is present, to which in each case an image value is assigned. In the following, three-dimensional images are considered, without any restriction of generality. The image values of the individual voxels are designated by $V_{x,z,y}^{(k)}$, index k indicating the iteration and x, y, z the position of the voxels within the examination object.

In step σ the local image noise of the image $Pic^k$ is estimated. A noise value $\sigma_{x,z,y}^{(k)}$ is thus determined for each voxel. Different methods for estimating noise can be used, e.g. the one described in document DE 10 2005 038 940 B4, the entire contents of which are hereby incorporated herein by reference. Here variances along certain lines running through the voxel are calculated for each voxel. The image values along a line are thus regarded as a statistical whole and the variance of this whole is calculated. Thus several one-dimensional variances are calculated in different spatial directions. The smallest of these variances is output as a result value $\sigma_{x,z,y}^{(k)}$ for the respective voxel at the location x, y, z. The reason for the use of the smallest value is that a large variance value is obtained for lines which run through edges or existing structures. $\sigma_{x,z,y}^{(k)}$ should not however identify the existence of structures in the vicinity of the respective voxel but provides a measure for the noise. In the case of the smallest variance value it can be assumed that this is typically characterized by noise and not by structure.

In step E an edge value $E_{x,z,y}^{(k)}$ is calculated for each voxel from the image $Pic^k$. To this end an edge-detecting filter is applied to the image $Pic^k$. For example, the use of the known Laplace filter K is suitable in accordance with.

$$E_{x,z,y}^{(k)} = (K * V^{(k)})_{x,z,y} := \sum_{j,m,n} K_{j,m,n} V_{x+j,y+m,z+n}^{(k)} \quad \text{Formula (1)}$$

Here $K*V^{(k)}$ means the performance of a three-dimensional convolution of the image $Pic^k$ with the Laplace filter K. An E-value $E_{x,z,y}^{(k)}$ is thus obtained for each voxel, a large E-value indicating the presence of an edge at the location x, y, z of the respective voxel.

In step β a voxel-dependent weighting function $\beta_{x,z,y}^{(k)}$ is determined from the noise value $\sigma_{x,z,y}^{(k)}$ and the edge value $E_{x,z,y}^{(k)}$. This is determined such that it has the attribute that it assumes values approaching 0 in the vicinity of edges, whereas in homogeneous areas of an image its values aspire to 1. Advantageously $\beta_{x,z,y}^{(k)}$ is defined by a Gaussian function:

$$\beta_{x,z,y}^{(k)} = \exp\left(-\left(\frac{E_{x,y,z}^{(k)}}{c_\beta \cdot \sigma_{x,z,y}^{(k)}}\right)^2\right) \quad \text{Formula (2)}$$

The selectable parameter $c_\beta$ permits sensitivity to be adjusted.

In homogeneous areas, thus where no edges are present, $E_{x,z,y}^{(k)}$ has small values, so that $\beta_{x,z,y}^{(k)}$ is approximately 1. In contrast $E_{x,z,y}^{(k)}$ has large values where edges are present, so that $\beta_{x,z,y}^{(k)}$ is very small. Because not $E_{x,z,y}^{(k)}$ but $$\frac{E_{x,y,z}^{(k)}}{\sigma_{x,y,z}^{(k)}}$$

is adopted, the Contrast to Noise Ratio (CNR) is taken into account locally. Because of the reference to $\sigma_{x,z,y}^{(k)}$ it is thus evaluated whether a significant structure or merely a high noise is present. Thus it is not simply the contrast which is reflected in the edge value $E_{x,z,y}^{(k)}$ which is of interest, but the ratio of contrast to noise.

In step U a smoothed image with image values $U_{x,z,y}^{(k)}$ is calculated from the image $Pic^k$. This can be effected by convolution with a three-dimensional low pass T, such as e.g. a Gaussian filter:

$$U_{x,z,y}^{(k)} = (T * V^{(k)})_{x,z,y} \quad \text{Formula (3)}$$

In step R a regularization image with image values $R_{x,z,y}^{(k)}$ is calculated from the image $Pic^k$ using $\sigma_{x,z,y}^{(k)}$:

$$R_{x,z,y}^{(k)} = \sum_{j,m,n} D_{j,m,n} G(V_{x+j,y+m,z+n}^{(k)} - V_{x,y,z}^{(k)}; \sigma_{x,y,z}^{(k)}) \quad \text{Formula (4)}$$

The operator D here represents a conventional high-pass which can be implemented e.g. by a Laplace filter. The influence function G weights the high-pass D depending on the difference between image values of the respectively considered voxel at the location x, y, z and the image values of the directly or more remotely adjacent voxels at the location x+j, y+m, z+n. It advantageously satisfies the attributes
G(−x)=−G(x), i.e. it is asymmetrical, and
G(ε)>0, i.e. for small positive values G is positive.

Using D would produce "normal" high-pass filtering of the image $Pic^k$. The influence function effects a deviation from the "normal" high-pass D, dependent on the CNR. The arguments of G are firstly the difference $V_{x+j,y+m,z+n}^{(k)} - V_{x,y,z}^{(k)}$ of image values. Secondly $\sigma_{x,z,y}^{(k)}$ is also used as an argument of G; it is advantageous to relate the difference in the image values to the local noise value, in order thereby to execute the regularization independently of the local noise. To this end the following is defined:

$$G(t; \sigma) = \sigma \cdot \tilde{G}\left(\frac{t}{\sigma}\right) \quad \text{Formula (5)}$$

A specific example of an influence function $\tilde{G}(t)$ is $$\tilde{G}(t) = \frac{t}{1 + \left(\frac{|t|}{c_0}\right)^p} \quad \text{Formula (6)}$$

Figure 4:
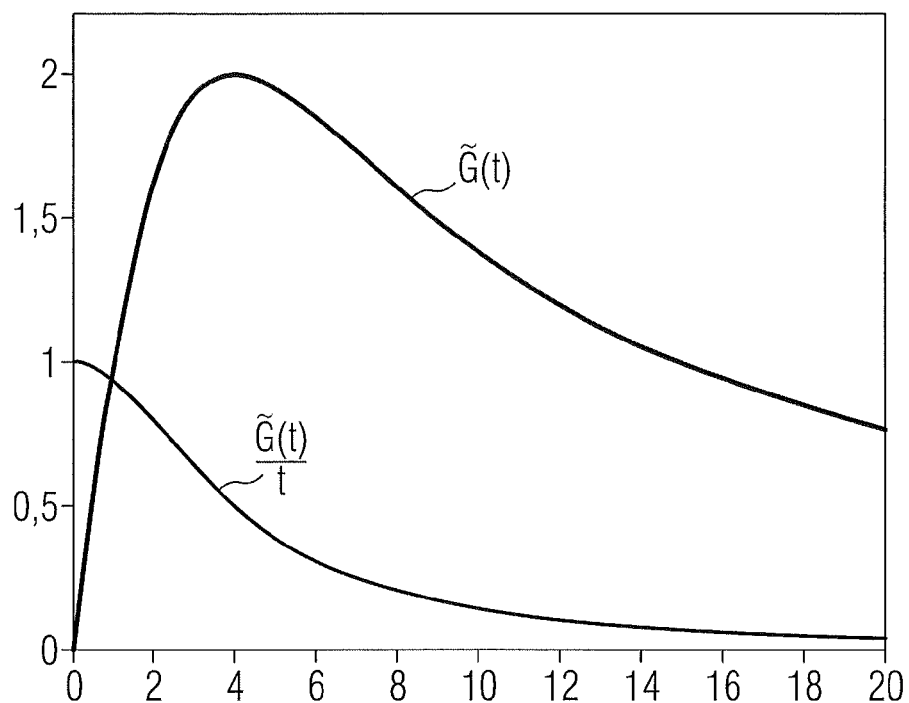
FIG. 4: a first influence function.

This is mapped in FIG. 4, with $c_0=4$ and p=2 being chosen. It is apparent that the influence function $\tilde{G}(t)$ at the start, i.e. in proximity to the value 0, is linear. In other words, voxels with a similar image value to the respectively considered voxel are used linearly in the high-pass; this corresponds to the "normal" use of the high-pass. As the argument increases—this corresponds to a larger value deviation between the image value of a voxel in relation to the image value of the respectively considered voxel at the location x, y, z—the influence function deviates from linearity: it initially ascends less than linearly, in order finally to actually descend. Falling G-values mean that the respective voxels are taken into account less in the high-pass calculation. Because $\sigma_{x,z,y}^{(k)}$ is also used in G, a high-pass filter effect is achieved, which decreases as a CNR increases.

The decrease in the high-pass effect is recognizable in FIG. 4 by the curve $$\frac{\tilde{G}(t)}{t}.$$

The more this curve deviates from the value 1, the more the influence function $\tilde{G}(t)$ deviates from linearity. In Formula (4) $c_0=4$ is the CNR in which the effect of the influence function on the value ½ has decreased, i.e. compared to a "normal" high-pass these voxels only contribute about half.

The effect of the influence function from FIG. 4 is thus that small and medium edges are contained in the high-pass filtered image, i.e. in the regularization image $R_{x,z,y}^{(k)}$, in accordance with high-pass filtering. In contrast, larger edges are taken little account of in high-pass filtering, so that they are scarcely visible in the regularization image $R_{x,z,y}^{(k)}$. The closer the influence function approaches the value 0, the more insignificant become the respective edges in the regularization image $R_{x,z,y}^{(k)}$.

It is even possible to select the influence function so that it changes its sign in the case of large arguments. An example of this is:

$$\tilde{G}(t) = \frac{t \cdot \left(1 - \frac{t}{c_1}\right)}{1 + \left(\frac{t}{c_0}\right)^p} \quad \text{Formula (7)}$$

Figure 5:
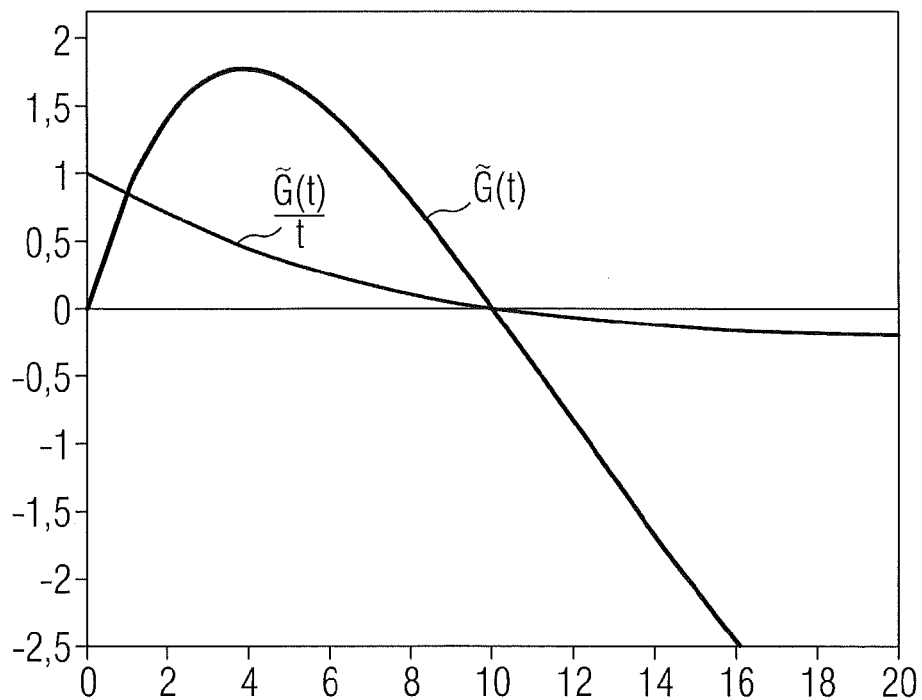
FIG. 5: a second influence function.

This function is illustrated for $c_0=4$, $c_1=10$ and p=1.5 in FIG. 5. If the influence function changes sign, this effects a change in the sign of the filter coefficient of the high-pass D. Thus high-pass filtering with negative signs takes place in respect of these large edges.

In principle the influence function should be chosen so that it initially ascends linearly, in order subsequently to ascend less than linearly. This deviation from the linear ascent can be so slight that the gradient of the influence function is still positive even for large arguments. The gradient can however also change its sign (see FIG. 4), and in this case the influence function too can change its sign (see FIG. 5).

In the next and final step of the current iteration the noise-reduced image $Pic^{k+1}$ is now calculated, the image $Pic^k$ being used first and the variables determined in steps U, R and β being used second. The following formula is used to calculate the image values of the image $Pic^{k+1}$:

$$V_{x,z,y}^{(k+1)} = V_{x,z,y}^{(k)} - \gamma^{(k)} \left[ \underbrace{\beta_{x,y,z}^{(k)} \cdot (V_{x,y,z}^{(k)} - U_{x,y,z}^{(k)})}_{(I)} + \underbrace{(1 - \beta_{x,y,z}^{(k)}) \cdot R_{x,y,z}^{(k)}}_{(II)} \right] \quad \text{Formula (8)}$$

The first part (I) in the square bracket represents a high-pass: U is a low-pass-filtered version of $V_{x,z,y}^{(k)}$, and subtracting it from the dataset $V_{x,z,y}^{(k)}$ produces a high-pass.

This first part (I) dominates the right side of the formula (8) in the homogeneous area of an image, i.e. in the area with $\beta_{x,z,y}^{(k)} \approx 1$. In this borderline case Formula (8) can be written as $$V^{(k+1)} \approx (1-\gamma^{(k)}+\gamma^{(k)}T)*V^{(k)} \qquad \text{Formula (9)}$$

This corresponds to low-pass filtering of the image $Pic^k$ (see Formula (3): T is a low-pass operator). As a result of this a smoothing of the image $Pic^k$ in the homogeneous area can thus be achieved. This makes it possible to adjust the noise power spectrum and thus permits direct control over the desired noise texture.

In contrast, in the areas of an image in which a significant structure was identified ($\beta_{x,z,y}^{(k)} \approx 0$), the second part (II) in the square bracket dominates the right side of Formula (8). In this borderline case Formula (8) can be written as $$V^{(k+1)} \approx V^{(k)} - \gamma^{(k)} R^{(k)} \qquad \text{Formula (10)}$$

Because the high-pass filtered regularization image $R^{(k)}$ is subtracted from the original image $V^{(k)}$ this corresponds to low-pass filtering. Those edges which because of the influence function were exempted from high-pass filtering, or at least were less affected, are accordingly also little affected by the low-pass filtering, if at all. These edges are thus left untouched during smoothing, and are thus retained slightly reduced or unchanged. For those edges for which because of the influence function a negative high-pass filtering was performed (see FIG. 5), subtracting the regularization image $R^{(k)}$ from the original image $V^{(k)}$ effects a high-pass filtering. These edges are thus even strengthened.

Overall the term (II) of Formula (8) thus corresponds to edge-selective filtering. A suitable influence function ensures that the edges are retained in the image or are even strengthened and thus no loss of contrast occurs.

The square bracket overall represents a version of the dataset $V_{x,z,y}^{(k)}$ filtered edge-selectively with a high-pass. Subtracting this bracket from $V_{x,z,y}^{(k)}$ produces a low-pass and thus a smoothing of the image $Pic^k$. Thus the result $V_{x,z,y}^{(k+1)}$ is smoothed while retaining the edges, as a result of which the noise was reduced. The overall effect can be controlled with the help of $\gamma^{(k)}$.

Thus after performing all steps within the dashed-line box a smoothed image $Pic^{k+1}$ is produced. This can be output as a results image, or can be subjected to fresh noise-reduction treatment. Preferably a particular number of iterations N is predefined, after which the procedure is terminated. Step k<N is used to check whether this number N of iterations has already been reached. If it has, in accordance with branch N, the most recently calculated image Pic is output as a results image. If not, then in accordance with branch Y the calculated image $Pic^{k+1}$ is subjected to a fresh iteration.

FIG. 6 shows a series of CT images which illustrate the effects of the various method steps in FIG. 3. FIG. 6A shows the initial image $Pic^0$. This is a two-dimensional sectional view through the thorax of a patient. The two circular structures disposed next to one another at the top are the right and left ventricles. The black volume to the right and left of the heart is the patient's lung. At the top edge of the image is the thorax, and above the thorax is a tube filled with contrast agent (white-filled circle).

Figure 6A:
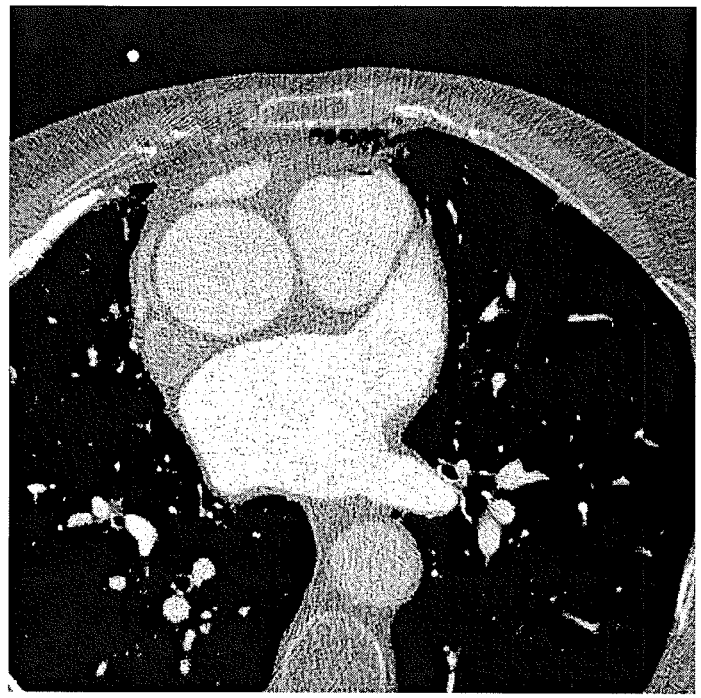
FIG. 6: a series of differently processed CT images.
Figure 6B:
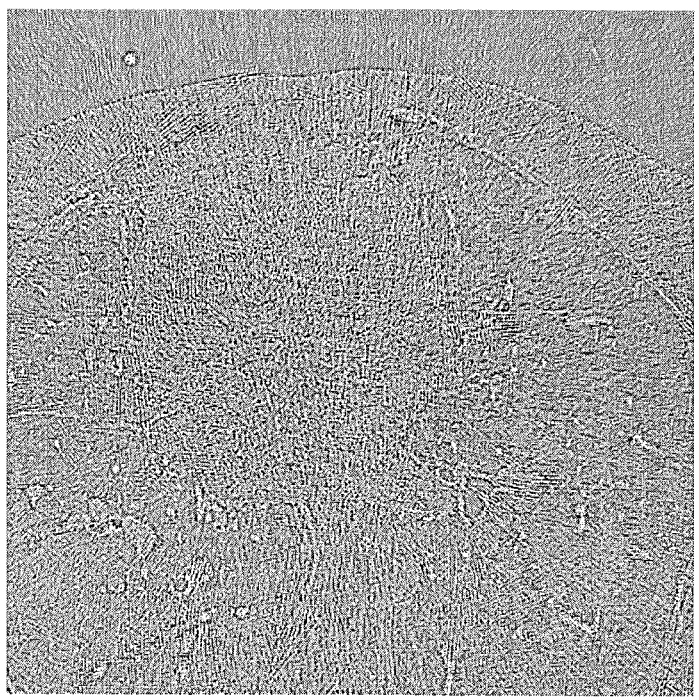

FIG. 6B shows the edge values $E_{x,z,y}^{(1)}$. This image shows at what points the edges, i.e. the structures, are located within the image in FIG. 6A.

Figure 6C:
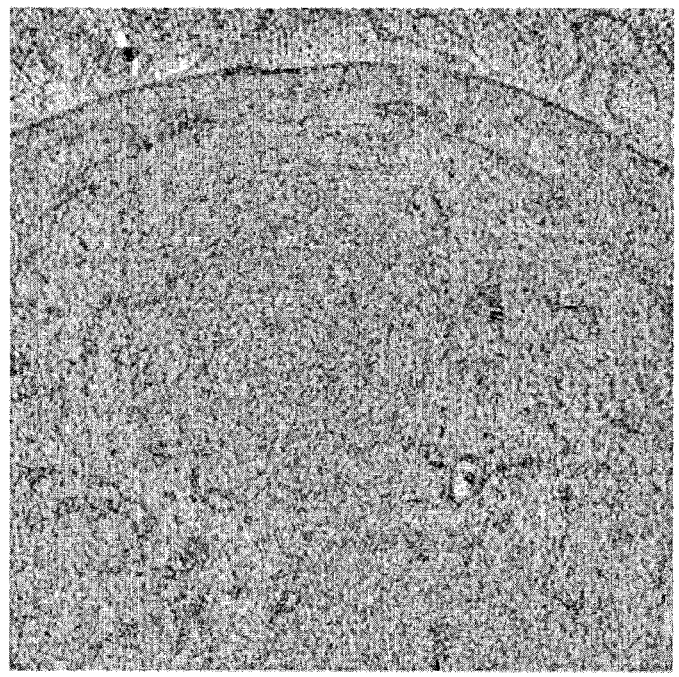

FIG. 6C shows the weighting function $\beta_{x,z,y}^{(1)}$. It is readily apparent that $\beta_{x,z,y}^{(1)}$ assumes small values (corresponding to dark grayscale levels) in the area of large variations in the image values of the image in FIG. 6A, whereas $\beta_{x,z,y}^{(1)}$ has larger values (corresponding to lighter grayscale levels) in homogeneous, structureless areas.

Figure 6D:
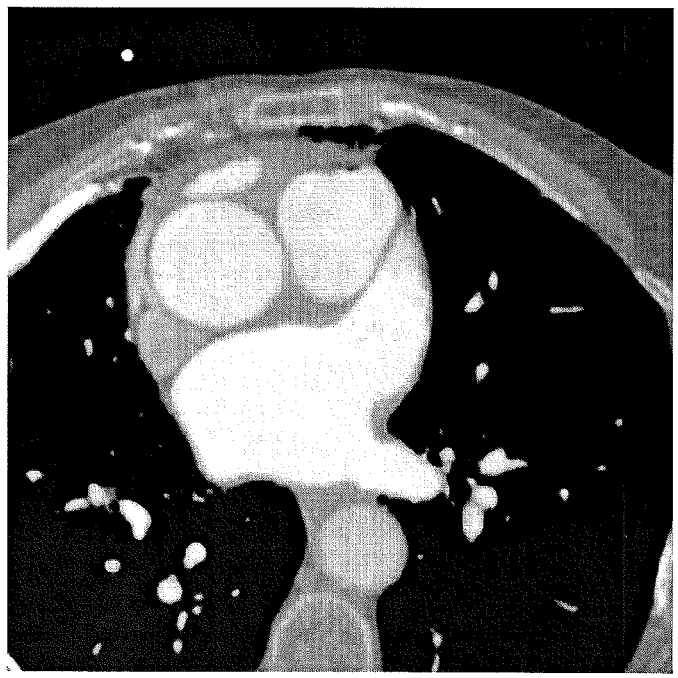

FIG. 6D shows the image values after the low-pass filtering of step U. Compared to the image in FIG. 6A the image in FIG. 6D is smoothed and thus has less noise, but is also less defined.

Figure 6E:
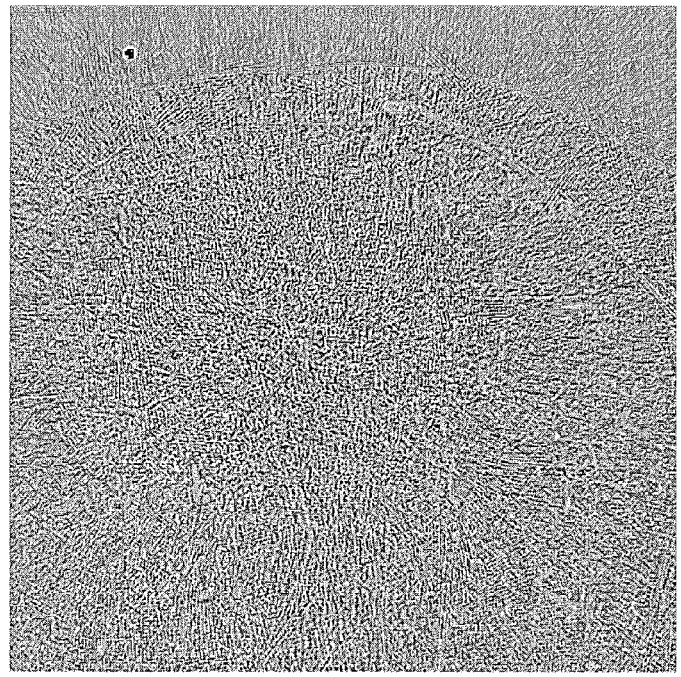

FIG. 6E shows the regularization image $R_{x,z,y}^{(1)}$. In contrast to the edge detector in FIG. 6B an edge-selective high-pass filter is present here, i.e. only several edges are subjected to high-pass filtering, whereas others have been used only to a lesser extent or not at all in the high-pass filtering. This is immediately apparent in that in FIG. 6E moderately distinct edges are not visible in contrast to the weak edges. Because of the construction of the influence function the filter effect of the high-pass is reduced when the differences in the pixel values are larger. In the example in FIG. 6 a function of the type in Formula (7) was selected, so that the effect of the high-pass is actually reversed when image value differences are large. Accordingly, very distinct edges are visible in FIG. 6E, but reversed compared to FIG. 6B. This can be seen from the wire which in FIG. 6B appears as a white dot with a black border, whereas in FIG. 6E it appears as a black dot with a white border. The final effect of this is that when comparing $Pic^k$ with $Pic^{k+1}$ moderate edges retain their original definition, whereas the definition of edges with a very high CNR is actually increased.

Figure 6F:
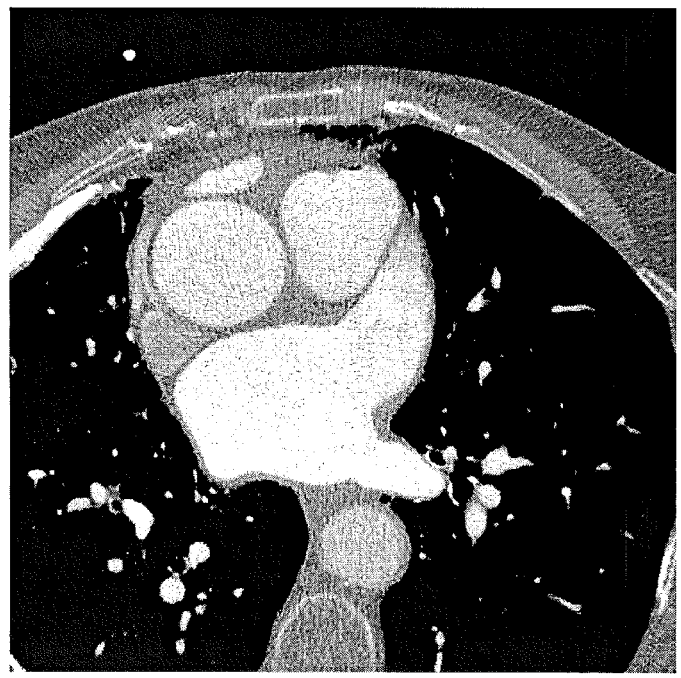

FIG. 6F shows the results image after the first iteration, which according to Formula (8) was calculated using the images in FIGS. 6A to 6E. Compared to FIG. 6A it shows a reduced noise combined with the same or even increased definition of structures.

If these steps are repeated several times, i.e. if several iterations are performed, the effects of both the noise reduction and the improved definition are increased. With 4 iterations the noise is reduced in this way by approx. 80%. This corresponds mathematically to the noise level of a measurement in the case of the 30-fold dose.

As already mentioned, the procedure described can also be applied to both two- and three-dimensional image data. In the case of three-dimensional image data the method should also be applied to this entire image dataset, and not just to each individual two-dimensional layer image. By including the third dimension better noise reduction is enabled during filtering than if only two-dimensional filtering were to be used.

The method can also be applied to 4-dimensional image data. In this case the fourth dimension is time. (The same of course applies if time represents the third dimension, thus a temporal sequence of two-dimensional images is present.)

The dimension of time is of interest in particular in the case of moving examination objects. A typical example of dynamic CT data is recordings of the beating heart, i.e. cardio-CT recordings, or CT perfusion measurements. In coronary CTA the coronary vessels are mapped in a rest phase of the heart, e.g. in the diastolic phase. The optimal phase can be determined e.g. by a motion analysis of a series of CT images. A four-dimensional image volume is obtained by reconstructing a temporal series of images of the three-dimensional heart volume in the vicinity of the optimal phase.

Besides the objectives explained above of effective noise reduction while retaining or increasing the image definition, the temporal definition, i.e. time resolution, is also now a variable to be considered. In smoothing filtering across several timepoints the time resolution deteriorates when using conventional methods. To reduce noise the reconstruction range could also be increased, i.e. measured data from a longer measurement interval is used for image reconstruction. However, this also necessarily reduces the temporal resolution of the images.

The deterioration in the temporal resolution when performing noise-reducing image smoothing in the dimension of time can be avoided by using the method explained above. In the case of dynamic CT measurements Formula (8) is modified as follows:

$$V_{t,x,z,y}^{(k+1)} = V_{t,x,z,y}^{(k)} - \gamma^{(k)}\left[\underbrace{\beta_{t,x,y,z}^{(k)} \cdot (V_{t,x,y,z}^{(k)} - U_{t,x,y,z}^{(k)})}_{(I)} + \underbrace{(1 - \beta_{t,x,y,z}^{(k)}) \cdot R_{t,x,y,z}^{(k)}}_{(II)}\right] \quad \text{Formula (11)}$$

The pixels $V_{t,x,z,y}^{(k)}$ are thus no longer present in three, but in four dimensions. This means that a sequence of images which correspond to different measuring timepoints is present as the initial image $Pic^0$.

As regards the effect of terms (I) and (II) the explanations for Formula (8) apply, with the difference that "edges" can now also occur in the time dimension. Unlike the spatial dimension, these do not correspond to physical structures, but to changes between images of different timepoints because of the motion.

The four-dimensional filterings must be performed in respect of each voxel of the volume that is of interest. This is very complex. To reduce the computing time, it is possible simply to obtain a single three-dimensional image, namely that of the optimum phase timepoint, as a results image. In this way the number of timepoints whose images are required for filtering in the time dimension is curbed. If the filter for example has the range 1 in the time dimension, i.e. a temporally adjacent image on each side of the image under consideration is required for high- or low-pass filtering, then for a four-fold iteration 9 temporally consecutive images would have to be allocated during the 0-th iteration, only 7 during the 1st iteration, only 5 during the 2nd iteration, and only 3 during the last iteration, in order hereby finally to output, as a smoothed results image which retains edges, the image situated temporally in the middle of the original 9 images.

The invention was described above using an example embodiment. It is clear that numerous changes and modifications are possible, without going beyond the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reconstruction of image data of an examination object from measured data, the measured data being captured during a relative rotational motion between a radiation source of a computed tomography system and the examination object, image data of the examination object being determined from the measured data and new image data being obtained by noise-reducing processing of the image data, the method comprising:

performing a weighted high-pass filtering of the image data, wherein the weighting takes account of differences between pixel values of different pixels such that increasing differences result in a weaker high-pass effect; and performing a noise-reducing smoothing of the image data using the weighted high-pass filtering.

2. The method as claimed in claim 1, wherein the new image data is obtained by processing the image data without using the measured data.

3. The method as claimed in claim 1, wherein the new image data is output as result image data.

4. The method as claimed in claim 1, wherein the new image data is thereafter subjected to noise-reducing processing.

5. The method as claimed in claim 1, wherein noise-reducing smoothing is performed using weighted high-pass filtering and wherein the high-pass filtered image data is subtracted from the image data.

6. The method as claimed in claim 1, wherein the weighting is performed by way of a function which initially ascends linearly and, as the argument increases, ascends weaker than linearly.

7. The method as claimed in claim 6, wherein the function initially ascends linearly and, as the argument increases, ascends weaker than linearly and, as the argument increases even more, descends.

8. The method as claimed in claim 6, wherein the function initially ascends linearly and, as the argument increases, ascends weaker than linearly and, as the argument increases even more, descends and, as the argument increases even more, changes its sign.

9. The method as claimed in claim 6, wherein the argument of the function contains the difference between pixel values of two pixels.

10. The method as claimed in claim 9, wherein the argument of the function contains the noise at one of the two pixels.

11. The method as claimed in claim 1, wherein a variable is determined pixel by pixel, and distinguishes between homogeneous areas and edges within the image data, and the variable decides pixel by pixel about the strength of use of the weighted high-pass filtering during noise-reducing smoothing of the image data.

12. The method as claimed in claim 11, wherein in addition to noise-reducing smoothing a low-pass filtering is performed, wherein the variable decides pixel by pixel about the strength of the low-pass filtering.

13. The method as claimed in claim 11, wherein the variable assumes values between 0 and 1, wherein the value 0 corresponds to an edge and the value 1 to a homogeneous area.

14. The method as claimed in claim 11, wherein for calculation of the variable, a high-pass filtering of the image data and a pixel-by-pixel noise value determination is performed.

15. The method as claimed in claim 14, wherein the variable is calculated by way of a Gaussian function which for each pixel depends on a quotient of a high-pass filtered pixel value and a noise value.

16. The method as claimed in claim 1, wherein the noise-reducing processing effects a contrast-dependent noise reduction of the image data.

17. The method as claimed in claim 1, wherein the image data is present as a temporal sequence of image data, and the noise-reducing processing is performed in the dimensions of both place and time.

18. A control and computing unit for reconstruction of image data of an examination object from measured data of a CT system, comprising:

a program memory for storing program code, wherein the program code performs the method according to claim 1 when executed.

19. A CT system comprising a control and computing unit as claimed in claim 18.

20. The method as claimed in claim 2, wherein the new image data is output as result image data.

21. The method as claimed in claim 2, wherein the new image data is thereafter subjected to noise-reducing processing.

22. The method as claimed in claim 7, wherein the argument of the function contains the difference between pixel values of two pixels.

23. The method as claimed in claim 8, wherein the argument of the function contains the difference between pixel values of two pixels.

24. The method as claimed in claim 12, wherein the variable assumes values between 0 and 1, wherein the value 0 corresponds to an edge and the value 1 to a homogeneous area.

25. A non-transitory computer readable medium including program segments for, when executed on a computer device, causing the computer device to implement the method of claim 1.

* * * * *